United States Patent [19]

Young

[11] Patent Number: 5,185,151

[45] Date of Patent: * Feb. 9, 1993

[54] PESTICIDAL COMPOSITIONS AND METHODS FOR CONTROLLING PESTS

[75] Inventor: Donald C. Young, Fullerton, Calif.

[73] Assignee: Union Oil Company of California, Los Angeles, Calif.

[*] Notice: The portion of the term of this patent subsequent to May 16, 2006 has been disclaimed.

[21] Appl. No.: 343,489

[22] Filed: Apr. 25, 1989

Related U.S. Application Data

[63] Continuation of Ser. No. 688,689, Jan. 3, 1985, Pat. No. 4,831,056, and a continuation-in-part of Ser. No. 453,496, Dec. 27, 1983, Pat. No. 4,910,179.

[51] Int. Cl.$^5$ .................................. A61K 31/10
[52] U.S. Cl. ........................ 424/400; 514/588
[58] Field of Search ................ 424/164; 514/588

[56] References Cited

U.S. PATENT DOCUMENTS

| | | |
|---|---|---|
| 1,340,708 | 5/1970 | Fjellanger . |
| 3,816,375 | 6/1974 | Bozer et al. . |
| 3,873,734 | 3/1975 | Higgins et al. . |
| 3,918,952 | 12/1975 | Neumiller . |
| 4,116,664 | 9/1978 | Jones . |
| 4,214,888 | 7/1980 | Young . |
| 4,310,343 | 1/1982 | Verdegaal et al. . |
| 4,315,763 | 2/1982 | Stoller et al. . |
| 4,397,675 | 8/1983 | Young . |
| 4,402,852 | 9/1983 | Young . |
| 4,404,116 | 9/1983 | Young . |
| 4,445,925 | 5/1984 | Young . |
| 4,447,253 | 5/1984 | Young . |
| 4,512,813 | 10/1984 | Young . |
| 4,522,644 | 6/1985 | Young . |
| 4,589,925 | 5/1986 | Young . |
| 4,626,417 | 12/1986 | Young . |
| 4,664,717 | 5/1987 | Young . |
| 4,673,522 | 6/1987 | Young . |
| 4,686,017 | 8/1987 | Young . |
| 4,722,986 | 2/1988 | Young . |
| 4,743,669 | 5/1988 | Young . |
| 4,755,265 | 7/1988 | Young . |
| 4,839,088 | 6/1989 | Young ..................... 502/167 |

Primary Examiner—Thurman K. Page
Assistant Examiner—P. Kulkosky
Attorney, Agent, or Firm—Gregory F. Wirzbicki; Michael H. Laird

[57] ABSTRACT

Pests are controlled by applying to the location of and/or to the path traversed by the pests a composition comprising urea and sulfuric acid in which the urea/$H_2SO_4$ molar ratio is less than 2. Novel compositions useful in such methods are also provided and comprise the described combinations of urea and sulfuric acid dispersed in a hydrocarbon oil. The novel method and compositions are particularly useful for controlling plant pests by applying the useful urea-sulfuric acid components to the plants or to the vicinity of plants occupied or traversed by such pests.

34 Claims, No Drawings

PESTICIDAL COMPOSITIONS AND METHODS FOR CONTROLLING PESTS

RELATED APPLICATIONS

This application is a continuation of application Ser. No. 688,689, filed Jan. 3, 1985, now U.S. Pat. No. 4,831,056 which is a continuation-in-part of my copending application, Ser. No. 453,496, filed Dec. 27, 1983 now U.S. Pat. No. 4,910,179.

BACKGROUND OF THE INVENTION

1. Field of the Invention

This invention relates to the field of pest control, and, in particular, it relates to compositions and methods useful for controlling pests, especially plant pests.

2. Description of the Art

A variety of plant pests are known to inflict significant damage to ornamental and crop plants and to periodically invade and thereby inconvenience residences and other structures and locations. Such pests typically include insects, gastropods, arachnids, worms, fungi, and plant pathogens such as viruses and bacteria. Such pests are generally controlled, if at all, with a variety of pesticides most of which are expensive, complex chemical compositions which are toxic to humans and/or the environment and which persist long after they are applied. Crop rotation is effective for controlling, although not eliminating, pests in several seasonal crops such as grasses, vegetables and grains and is much less innocuous than is the use of chemical pesticides. However, crop rotation serves only to reduce rather than eliminate pest populations and, of course, cannot be employed in perennial crops. Obviously, such methods of pest control suffer from numerous disadvantages including expense of the compositions or procedures (crop rotation) involved, threats to the environment which are presented by persistent chemical pesticides, and hazards to humans involved in the manufacture, transportation and application of such pesticides and to consumers of produce from pesticide-treated crops.

Sulfuric acid is known to be effective for controlling pests, and it kills essentially all pests upon contact. However, sulfuric acid is seldom used for such purposes due to its corrosivity and reactivity with almost every material which it contacts including human skin, clothing, and essentially all substrates to which it would be applied for pest control. Furthermore, sulfuric acid rapidly reacts by oxidation, dehydration, and/or sulfonation with protenatious matter and other matter of pest anatomy and with substrates such as wood bark, dormant grasses, etc. to which it might be applied to control pests, and it is consumed by such reactions. Jones, U.S. Pat. No. 4,116,664 and Verdegaal et al., U.S. Pat. No. 4,310,343, disclose that this chemical activity or sulfuric acid can be attenuated by reacting it with urea to form a variety of urea-sulfuric acid formulations which are useful as liquid fertilizers. Jones teaches that the resulting urea-sulfuric acid combinations are nontoxic, noncaustic, and noncorrosive to black iron and, accordingly, can be safely transported, handled, stored, and applied by ordinary farm workers and ordinary application equipment due to the absence of the chemical reactivity which is characteristic of sulfuric acid per se.

SUMMARY OF THE INVENTION

I have now found that a variety of pests can be controlled by applying to a location occupied or traversed by such pests a composition comprising a combination of urea and sulfuric acid in which the urea/$H_2SO_4$ molar ratio is below 2. Without being constrained to any particular theory of this invention, it is presently believed that urea-sulfuric acid compositions in which the urea/$H_2SO_4$ molar ratio is below 2 contain, and/or will generate, the monourea adduct of sulfuric acid, and that this adduct, rather than the diurea adduct of sulfuric acid, which forms at urea/$H_2SO_4$ molar ratios of 2 and above, retains the substantial protenating activity of sulfuric acid and therefore is pathogenic to life forms and to a variety of pests in particular. Compositions which comprise a combination of a hydrocarbon oil, urea, and sulfuric acid in which the urea/$H_2SO_4$ molar ratio is below 2 are particularly useful for controlling pests and for eliminating the deleterious effects that such pests otherwise have in various environments, including their negative effects on ornamental and crop plants.

The methods and compositions of this invention have a number of advantages over known methods and compositions for controlling pests. The useful compositions are less expensive than most, if not all, effective pesticides. They are effective on contact and are nontoxic to the environment and to plants and therefore can be repeatedly applied as required. In fact, the useful compositions are beneficial both to the environment and to plants since they are converted to useful fertilizers and soil adjuvants. They are nonpersistent in the sense that they do not remain toxic even to controlled pests for prolonged periods of time, yet they are sufficiently persistent to afford adequate control of the desired pests. Depending on the manner of application, the useful compositions can remain effective against pests for 2 to 4 weeks or more in some circumstances unless removed from the area to which they are applied by washing or are deactivated by neutralization; and the useful compositions are readily and inexpensively deactivated by neutralization with readily available bases such as ammonia, ammonium hydroxide, sodium hydroxide, etc. They are less hazardous to surfaces and plants to which they are applied than is sulfuric acid, and they also are less hazardous to applicators and less detrimental to application equipment than is sulfuric acid. Yet the useful compositions are more stable than sulfuric acid and therefore maintain their pesticidal activity for a longer period of time since they do not react with most substances to which they are applied by oxidation, dehydration, and sulfonation as does sulfuric acid.

DETAILED DESCRIPTION OF THE INVENTION

This invention provides methods useful for controlling pests which involve applying to locations occupied and/or traversed by the controlled pests a composition comprising urea and sulfuric acid in which the urea/$H_2SO_4$ molar ratio is below 2. Novel pesticidal compositions are also provided, and these involve combinations of urea, sulfuric acid, and a hydrocarbon oil in which the urea/$H_2SO_4$ molar ratio is below 2.

The pests which can be controlled by the methods and compositions of this invention include a wide variety of species which typically are detrimental to plants and/or which often invade residences or other structures. Treatable pests include mobile and immobile pests such as flying, windblown, and crawling insects and other pests including viruses and bacteria which are carried by other vectors such as insects and windblown soil or plant matter. Typically, such pests include insects, gastropods, arachnids, worms, fungi, viruses, and bacteria. Illustrative insects include so-called sucking bugs such as members of the genus Lygus, homopterous insects such as aphids and scale, hoppers such as tree, leaf, and grasshoppers, insects of the order Coleopetera including beetles and weevils, insects of the order Dermoptera including earwigs, ants, thrips, crickets and numerous others. Illustrative gastropods include pulmonate gastropods such as slugs and gastropod mollusks including all varieties of snails. Typical worm pests include the larvae of moths and other insects (including caterpillars), grubs, web worms, canker worms, etc. Typical arachnids include detrimental spiders and mites such as spider mites, brown mites, rust mites, etc., which are known to be principle carriers of disease vectors (pathogens) between plants and/or between the plants and soil. Pathogens which can be controlled by the methods and compositions of this invention include viruses which are exposed on the surface of the soil or other treated surfaces or on the woody parts of plants, or which are carried by mobile disease vectors such as the arachnids, sucking bugs, and other pest forms referred to above. Other controllable pathogens include bacteria, particularly the rhizobia bacteria which exist principally in the root zone of plants near the surface, particularly in the root zones of grass crops, and fungi including saprophytic and parasitic power plants such as molds, rusts, mildews, smuts, and the like.

The compositions which are useful in this invention contain urea-sulfuric acid components in which the urea/$H_2SO_4$ molar ratio is below 2. These compositions may optionally contain water, and it is the combination of water with the urea-sulfuric acid component which is believed to constitute the effective pesticidal agent. Without being constrained to any particular theory of this invention, it is believed that the monourea adduct of sulfuric acid is the most effective and persistent pesticidal component of these compositions. The monourea adduct exists only in urea-sulfuric acid components which have urea/$H_2SO_4$ molar ratios below 2. Thus, it is generally preferable to provide that the urea-sulfuric acid component contain a significant proportion of the monourea adduct of sulfuric acid. Furthermore, it is desirable to minimize the deleterious effects associated with the presence of free (unadducted) sulfuric acid in the urea-sulfuric acid component. Taking these factors into consideration, the useful urea-sulfuric acid components usually have urea/$H_2SO_4$ molar ratios within the range of about $\frac{1}{4}$ to less than 2, generally about $\frac{1}{4}$ to about 7/4, and preferably at least about $\frac{1}{2}$, the latter of which assures that at least 50 percent of the sulfuric acid will be present as adducted sulfuric acid. The deleterious effects of free sulfuric acid can be minimized or eliminated altogether by employing urea-sulfuric acid components in which the urea/$H_2SO_4$ molar ratio is at least about 1. Thus, it is sometimes preferable to employ urea-sulfuric acid components which have urea/$H_2SO_4$ molar ratios within the range of about 1 to less than 2.

The concentration of the urea-sulfuric acid component in the pesticidal compositions useful in this invention should be sufficient to control the treated pest and/or to inhibit the detrimental activity of such pests either toward plants or otherwise. Very low concentrations of the useful urea-sulfuric acid components are sufficient to achieve at least some degree of control and/or inhibition of treated pests. Furthermore, the urea-sulfuric acid component can be applied in very dilute form, e.g., an aqueous solution, from which the water or other solvent evaporates, thereby increasing the effective concentration of the urea-sulfuric acid component on the treated substrate. Typically, the urea and sulfuric acid, in combination, will constitute at least about 0.5 and generally at least about 5 weight percent of the useful compositions. Compositions which contain higher proportions of urea and sulfuric acid are even more effective for immediate pest control. Thus, the urea-sulfuric acid concentration can vary considerably, and the urea and sulfuric acid can, in combination, constitute about 1 to about 90 weight percent, most often 1 to about 50 weight percent of the composition as applied. Generally speaking, increasing the urea-sulfuric acid component concentration increases effectiveness.

Particularly useful urea-sulfuric acid components for immediate control of contacted pests are aqueous solutions of the urea-sulfuric acid components in which the $H_2O/(urea+H_2SO_4)$ molar ratio is less than about 2.5. In such compositions the urea and sulfuric acid, in combination, will constitute at least about 60 weight percent of the composition based on the combined weight of urea, sulfuric acid, and water.

The useful compositions can contain any one or more of a variety of other materials which do not inhibit or negate the pesticidal activity of the urea-sulfuric acid components to an unacceptable extent. Illustrative of such additional components are nutrients such as potassium, phosphorus, and micronutrients (magnesium, copper, etc.) which can be present as oxides or other compounds such as potassium hydroxide, phosphoric acid, ammonium phosphate, etc.

The novel compositions of this invention are combinations of the described urea-sulfuric acid components with a hydrocarbon spray oil which, at the temperature at which it is applied, has a viscosity which is sufficiently low to allow adequate distribution. These compositions usually involve emulsions of the spray oil and an aqueous urea-sulfuric acid component in which either the water phase or hydrocarbon phase can constitute the discontinuous phase. The hydrocarbon oil increases the pesticidal effectiveness and persistence of the urea-sulfuric acid components, particularly for the treatment of pests and/or surfaces which are not readily wet by water. The hydrocarbon-containing components are also useful for treating areas which are exposed to water which might otherwise rapidly wash the pesticidal urea-sulfuric acid component from the treated pest or surface.

Typically, the useful hydrocarbon oils will have melting points below about 10° C. and usually constitute petroleum oils. The hydrocarbon oil can be either pesticidal, e.g., herbicidal and/or insecticidal, or not. Therefore, both aromatic and non-aromatic, sulfonated and unsulfonated hydrocarbon oils can be employed. Paraffinic (non-aromatic) spray oils are preferred for the treatment of areas or plants when it is preferable to avoid herbicidal effects or persistent pesticidal effects associated with other spray oils such as the sulfonated and highly aromatic spray oils. Paraffinic spray oils are generally characterized as those which contain less than 7 volume percent aromatics, and they typically have viscosities within the range of about 60 to about 150 Saybolt seconds.

The novel hydrocarbon-containing urea-sulfuric acid compositions typically contain about 2 to about 60, preferably about 10 to about 60, and most preferably about 20 to about 40 weight percent of the urea-sulfuric acid component expressed as the combined weight of urea and sulfuric acid and based on the total weight of the composition. The hydrocarbon oil typically constitutes at least about 10 weight percent, and generally at least about 30 weight percent of the composition. However, oil content can vary considerable since very minor oil concentrations e.g., about 5 weight percent, are adequate to produce some afford greater beneficial effect. Higher oil concentrations afford greater persistence and effectiveness, particularly when applied to water repellent pests and/or treated surfaces. Thus, the oil concentration will usually be within the range of about 10 to about 98 weight percent, generally about 40 to about 90 weight percent based on the total weight of the composition.

The water concentration of the novel compositions need only be sufficient to act as an adequate carrier for the urea-sulfuric acid component. Thus, due to the high solubility of the urea-sulfuric acid components in water, very minor water concentrations can be employed when the concentration of the urea-sulfuric acid component is relatively low. Accordingly, the water content of the novel compositions can be as low as about 1 weight percent but is preferably at least about 5 weight percent of the total composition. However, much higher water concentrations also can be employed. Thus, water concentration is typically within the range of about 5 to about 80, generally about 10 to about 50 weight percent based on the combined weight of urea, sulfuric acid, and water.

In addition to influencing the maximum urea-sulfuric acid component concentration that can be carried by the novel pesticidal compositions, water concentration also influences the stability of the water-hydrocarbon emulsion. For instance, when the hydrocarbon phase is the continuous phase of the emulsion (which is preferable for immediate wetting of hydrophobic pests or substrates) the water concentration is preferably below about 20 weight percent based on the total weight of the composition. When the water concentration is increased, e.9., to about 50 percent or more of the total composition, the water-in-oil emulsions (if used as a starting material) will invert to oil-in-water emulsions which can be stabilized by the addition of typical surfactants, e.g., emulsifiers, stabilizers, etc.

In addition to stabilizing the novel oil-in-water emulsions, surfactants also aid in the control of pests located on woody plant parts. However, surfactants are generally not preferred for the treatment of sensitive plant parts, especially foliage, since they accentuate the herbicidal activity of the urea-sulfuric acid components as described in my copending application Ser. No. 444,667, Methods for Controlling Vegetation, filed Nov. 26, 1982, the disclosure of which is incorporated herein by reference in its entirety.

The novel hydrocarbon-containing pesticidal compositions of this invention can be readily prepared by mixing the hydrocarbon oil, urea-sulfuric acid component and water and subjecting the combination to high shear mixing. For instance, either the oil-in-water or water-in-oil emulsions can be readily prepared in a Waring blender. Of course, larger commercial scale equipment is generally preferred for the manufacture of commercial quantities.

The useful urea-sulfuric acid components can be prepared by any procedures which is capable of forming the described combinations of urea and sulfuric acid. Particularly preferred methods are discussed in my U.S. Pat. Nos. 4,397,675, "Method of Producing Urea-Sulfuric Acid Reaction Products," and 4,445,925, "Methods of Producing Concentrated Urea-Sulfuric Acid Reaction Products," the disclosures of which are incorporated herein in their entirety. The methods disclosed in my noted U.S. patents are particularly useful for the preparation of urea-sulfuric acid components which are free of decomposition products of urea, sulfuric acid, and/or the mono/or diurea adducts such as ammonium sulfate, sulfamic acid, and ammonium sulfamate which can result from the use of other manufacturing procedures. Useful noncorrosive urea-sulfuric acid components which are preferable for use in transportation, mixing and/or application equipment which is subject to corrosion, are described in my U.S. Pat. Nos. 4,402,852, "Noncorrosive Urea-Sulfuric Acid Compositions," and 4,404,116, "Noncorrosive Urea-Sulfuric Acid Reaction Products," the disclosures of which are incorporated herein in their entireties.

The methods and compositions of this invention can be employed to control pests by application of the useful urea-sulfuric acid components to plants, soils (particularly in the vicinity of plants), sidewalks, residences, and/or other structures or sites. They are particularly useful for the control of pests located on or which traverse the woody portions of plants such as deciduous and coniferous, fruiting, timber, and/or ornamental trees, vines, and bushes including almond trees, citrus, pines, junipers, grapes and other berry vines, and the like. These methods and compositions are also useful for the control of pests in dormant grasses such as alfalfa and grass seed crops such as rye, fescue, bermuda, blue grass and the like by the application of the useful urea-sulfuric acid components to such dormant crops. They also can be employed to control pests on the foliage of resistant xerophytic plants such as onions, garlic, broccoli, and other xerophytic species, the foliage of which is resistant to the herbicidal effect of the urea-sulfuric acid component (in the absence of surfactants).

Pests located on or which traverse the soil surface, particularly in the vicinity of plants, also can be controlled by the novel methods and compositions of this invention. However, the sulfuric acid constituent of the urea-sulfuric acid components is neutralized upon contact with basic soil components. Accordingly, the application of the useful urea-sulfuric acid components directly to soil may result only in the control of pests which are immediately contacted with the active component. The useful urea-sulfuric acid components persist much longer on organic matter on the soil surface such as the duff which usually exists in the immediate vicinity of ornamental and crop plants such as on orchard floors, vineyards, and in dormant grass crops. Thus, the urea-sulfuric acid components provide residual control of pests located in or which traverse such organic matter.

In accordance with the methods of this invention, pests are controlled by applying a pesticidally effective amount of the described urea-sulfuric acid components to the location of and/or to the path traversed by the pests. The amount of the urea-sulfuric acid component applied should be sufficient to at least inhibit the detrimental activity of the controlled pest. Dosage rates usually correspond to at least about 40 pounds per acre, generally about 80 to about 800 pounds per treated acre (based on the combined weight of urea and sulfuric acid) when topical application is employed. When it is desired to control pests located on or which traverse the woody portions of plants or the duff at the plant's base, the urea-sulfuric acid components should be applied at a rate sufficient to at least partially wet the treated surface.

Application timing should be correlated with the presence and/or migratory behavior of the controlled pests. Contact control of active and dormant pests located on the treated site can be effected by the application of the useful urea-sulfuric acid component to the pests in the treated location. Pests which migrate either daily or annually can also be controlled by these methods. Thus, nocturnal ground-dwelling pests, such as cut-worms, can be controlled by applying to the base or woody stalk or trunk of the affected plants a pesticidally effective amount of the useful urea-sulfuric acid components. The soil dwelling pests will either avoid migrating through the treated area or will be inhibited or killed upon contact with the urea-sulfuric acid component.

Since the useful urea-sulfuric acid components have 2 to 4 weeks residual control, particularly when applied to the woody parts of plants (if not washed off or neutralized), one application is often adequate to control treated pests due to the relatively short life cycle of many pest varieties. However, pests which are more persistent, either due to longer life cycles or otherwise, can be controlled by repeated applications of the useful components. Annually migrating pests which winter in the organic material, i.e., duff, at the base of plants can be controlled by applying the urea-sulfuric acid components to the surface of the organic material at the plant's base and/or to the woody portion of the plant immediately prior to or during the pest migration. The best control is usually achieved in early spring when surface warming initiates pest reemergence from the soil and migration to the plant.

The invention is further described by the following examples which are illustrative of specific modes of practicing the invention and are not intended as limiting the scope of the invention as defined by the appended claims.

EXAMPLE 1

The trunks of almond trees which are normally infested with mites during the spring and summer are sprayed from ground level up to a height of several feet with a sufficient amount of a composition containing 36.4 weight percent urea, 52.1 weight percent sulfuric acid and 11.5 weight percent water to dampen the tree bark. The composition has a urea/$H_2SO_4$ molar ratio of 1.1. The application is made in early spring at the first warming and shortly before the reemergence of mites which winter in the soil. Following mite reemergence and the mite infestation of untreated trees in the same population, the treated almond trees are found to be free of mite infestations.

EXAMPLE 2

The trunks of citrus trees are treated with the urea-sulfuric acid component described in Example 1 by applying a sufficient quantity of the urea-sulfuric acid component to wet the trunk bark from approximately ground level to a height of several feet. The urea-sulfuric acid component is applied shortly before mite reemergence in the early spring. The treated citrus trees remain free of mite infestation. In contrast, untreated trees in the same population evidence mite infestations.

EXAMPLE 3

The woody lower vine portions of trellised grape plants are sprayed with a sufficient quantity of the urea-sulfuric acid component described in Example 1 to wet the bark from soil level to a height of approximately 2 feet. The spray is applied immediately prior to mite reemergence from the soil in early spring. The treated plants show no signs of mite infestations, while untreated grape plants in the same population are infested with mites.

EXAMPLE 4

Scale on the limbs of dormant walnut trees is killed by spraying the infested stems with a sufficient quantity of the urea-sulfuric acid component described in Example 1 to wet the stem bark. The scale infestation dies immediately as indicated by a marked color change to a bleached skeleton after which the scale falls from the affected plant portions. All evidence of scale infestation is gone within 24 hours.

While particular embodiments of this invention have been described, it will be understood, of course, that the invention is not limited thereto since many obvious modifications can be made, and it is intended to include within this invention any such modifications as will fall within the spirit and scope of the appended claims.

Having described my invention, I claim:

1. A pesticidal composition comprising a pesticidally effective amount of the monourea adduct of sulfuric acid and a hydrocarbon oil.

2. The composition defined in claim 1, which comprises at least about 5 weight percent water, said adduct constitutes at least about 2 weight percent of said composition and said oil has a melting point of about 10° C. or below.

3. The composition defined in claim 2, which comprises an emulsion of a water phase and an oil phase, and said water phase is the discontinuous phase of said emulsion.

4. The composition defined in claim 2, which comprises an emulsion of a water phase and an oil phase, and said water phase is the continuous phase of said emulsion.

5. The composition defined in claim 1, wherein said adduct constitutes about 2 to about 60 weight percent of said composition and said composition comprises about 5 to about 80 weight percent water and an emulsion of a water phase and a hydrocarbon oil phase and is essentially free of surfactant.

6. The composition defined in claim 5, wherein said hydrocarbon oil constitutes at least about 5 weight percent of said composition, and said composition is free of sulfuric acid.

7. The composition defined in claim 5, wherein said hydrocarbon oil is the continuous phase of said emulsion.

8. The composition defined in claim 1, wherein said adduct constitutes at least about 0.5 weight percent of said composition, and said composition comprises at least about 1 weight percent water and a water-hydrocarbon oil emulsion.

9. The composition defined in claim 8, which further comprises a surfactant.

10. The composition defined in claim 1, wherein said hydrocarbon oil is a paraffinic petroleum oil having a melting point of about 10° C. or below, and said composition is free of unadducted sulfuric acid.

11. A pesticidal composition comprising a pesticidally effective amount of the monourea adduct of sulfuric acid and at least about 5 weight percent of a hydrocarbon oil, which composition is free of unadducted sulfuric acid.

12. A fungicide comprising a hydrocarbon oil and a fungicidally effective amount of the monourea adduct of sulfuric acid.

13. The composition defined in claim 12 which further comprises a surfactant.

14. A method for controlling pests which method comprises the step of applying to the location occupied or traversed by said pests a pesticidally effective amount of a composition comprising the monourea adduct of sulfuric acid.

15. The method defined in claim 14, wherein said composition further comprises a hydrocarbon oil.

16. The method defined in claim 14 wherein said composition is applied to a location traversed by said pests.

17. The method defined in claim 14 wherein said composition is applied to a dormant grass crop.

18. The method defined in claim 14 wherein said pests are selected from the group consisting of insects, gastropods, arachnids, worms, fungi, viruses, bacteria, and combinations thereof.

19. The method defined in claim 14 wherein said composition comprises a hydrocarbon oil and is applied to organic matter on the soil surface in the vicinity of plants which are to be protected from said pests.

20. A method for controlling pests which comprises applying to a location occupied or traversed by said pests a composition having pesticidal activity which composition comprises a hydrocarbon oil, and a pesticidally effective amount of the monourea adduct of sulfuric acid.

21. The pesticidal composition defined in claim 1 free of unadducted sulfuric acid.

22. The fungicide defined in claim 12 free of unadducted sulfuric acid.

23. A method for controlling fungi which comprises applying to said fungi a fungicidally effective amount of a composition comprising the monourea adduct of sulfuric acid.

24. The method defined in claim 23 wherein said fungi are selected from the group consisting of molds, rusts, mildews, smuts, and combinations thereof.

25. The method defined in claims 14 or 23 wherein said composition comprises an amount of hydrocarbon oil sufficient to increase the persistence of said composition when applied.

26. The method defined in any one of claims 14, 20 or 23 wherein said composition comprises at least about 5 weight percent water, said adduct constitutes at least about 2 weight percent of said composition expressed as the weight of combined equivalent urea and sulfuric acid, and at least about 5 weight percent of a hydrocarbon oil.

27. The method defined in claim 26 wherein said composition comprises an emulsion of a water phase and an oil phase, and said water phase is the discontinuous phase of said emulsion.

28. The method defined in claim 25 wherein said composition comprises an emulsion of a water phase and an oil phase, and said water phase is the continuous phase of said emulsion.

29. The method defined in any one of claims 14, 20 or 23 wherein said composition comprises about 2 to about 60 weight percent of said adduct expressed as the weight of combined equivalent urea and sulfuric acid, at least about 5 weight percent of a hydrocarbon oil, and about 5 to about 80 weight percent water, and comprises an emulsion of a water phase and a hydrocarbon phase.

30. The method defined in any one of claims 14, 20 or 23 wherein said adduct constitutes at least about 0.5 weight percent of said composition, and said composition comprises at least about 1 weight percent water and a water-hydrocarbon oil emulsion.

31. The method defined in claim 30 wherein said composition further comprises a surfactant.

32. The method defined in any one of claims 14, 20 or 23 wherein said composition comprises a paraffinic oil having a melting point of about 10° C. or less, and said composition is free of unadducted sulfuric acid.

33. The method defined in any one of claims 14, 20 or 23 wherein said composition is applied to organic matter on the soil surface.

34. The composition defined in claim 1 comprising an amount of said adduct sufficient to kill a member selected from the group consisting of insects, gastropods, arachnids, worms, fungi, and combinations thereof.

* * * * *

UNITED STATES PATENT AND TRADEMARK OFFICE
CERTIFICATE OF CORRECTION

PATENT NO. : 5,185,151

DATED : February 9, 1993

INVENTOR(S) : Donald C. Young

It is certified that error appears in the above-identified patent and that said Letters Patent is hereby corrected as shown below:

Title Page, item [56], under "References Cited," column 2, between
"4,839,088 6/1989 Young .............502/167" and "Primary Examiner--
Thurman K. Page" insert
-- OTHER PUBLICATIONS The Condensed Chemical Dictionary, Seventh Edition, Van Nostrand
Reinhold Company, New York, 1969, p. 908.
D. F. du Toit, Verslag Akad. Wetenschappen, 22,573-4 [Abstracted in
Chemical Abstracts, 8, 2346, (1914).]
L. H. Dalman, "Ternary Systems of Urea and Acids, I. Urea, Nitric Acid
and Water, II. Urea, Sulfuric Acid and Water, III. Urea, Oxalic Acid and
Water"; JACS, 56, 549-53 (1934).
Sulfur Institute Bulletin, No. 10 (1964), "Adding Plant Nutrient Sulfur to
Fertilizer".
Title 40, Code of Federal Regulations, Section 180.1019, "Sulfuric Acid;
Exemption from the Requirement of Tolerance."
Adalla, "Effects of Herbicidal Weed Control on Growth and Development
of Ground Nuts (Arachis Hypogaea I>) in Western Kenya," Proceedings
of the East African Weed Science Conf., 6, 1976, published 1977; Chemical
Abstract 93, 93:90069b, 1980. (Only the abstract is cited.)
Bach et al., "Destroying Potato Plants," East German Patent 146,541,
February 18, 1981, Chemical Abstract, 95, 95:37118g (1981). (Only the
abstract is cited.) --

Title page, item [57], "ABSTRACT," line 7, after "novel" replace "method"
with -- methods --.

Column 8, claim 6, line 59, after "free of" insert -- unadducted --.

UNITED STATES PATENT AND TRADEMARK OFFICE
CERTIFICATE OF CORRECTION

PATENT NO. : 5,185,151

DATED : February 9, 1993

INVENTOR(S) : Donald C. Young

It is certified that error appears in the above-indentified patent and that said Letters Patent is hereby corrected as shown below:

Column 10, claim 28, line 21, repalce "25" with --26--.

Signed and Sealed this

Seventh Day of March, 1995

Attest:

BRUCE LEHMAN

Attesting Officer          Commissioner of Patents and Trademarks